(12) United States Patent
Presnell et al.

(10) Patent No.: US 6,500,928 B1
(45) Date of Patent: Dec. 31, 2002

(54) MAMMALIAN CYTOKINE-LIKE FACTOR 7

(75) Inventors: Scott R. Presnell, Tacoma, WA (US); Teresa Gilbert, Seattle, WA (US); Theresa Martinez, Greenbank, WA (US); Ross C. Hoffman, San Diego, CA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/620,956

(22) Filed: Jul. 21, 2000

Related U.S. Application Data

(63) Continuation of application No. 09/066,745, filed on Apr. 24, 1998, now abandoned.
(60) Provisional application No. 60/071,676, filed on Jan. 16, 1998, and provisional application No. 60/044,886, filed on Apr. 25, 1997.

(51) Int. Cl.$^7$ .......................... C07K 14/52; C12N 5/10; C12N 15/19; C12N 15/63

(52) U.S. Cl. .................... 530/351; 536/23.5; 435/69.5; 435/471; 435/320.1; 435/252.3

(58) Field of Search ................... 530/350, 351; 536/23.1, 23.5; 435/69.1, 69.5, 71.1, 71.2, 471, 325, 320.1, 252.3, 254.11

(56) References Cited

PUBLICATIONS

Hillier et al., The Wash U–Merck EST Project, 1996.
Marra et al., The Wash U–Merck EST Project, 1996.
Zheng et al., Path. Res. Pract. 188: 1104–1121, 1992.
Hillier et al., The Wash U–Merck EST Project, 1995.
Marra et al., WashU–HHMI Mouse EST Project, 1996.

*Primary Examiner*—Prema Mertz
(74) *Attorney, Agent, or Firm*—Paul G Lunn

(57) ABSTRACT

Novel mammalian zcyto7 polypeptides, polynucleotides encoding the polypeptides, and related compositions and methods including antibodies and anti-idiotypic antibodies.

2 Claims, No Drawings

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 736 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 57...596
      (D) OTHER INFORMATION:

(xi) SEQUENCE DESCRIPTION: SEQ ID NO: 1:

```
GAATTCGGCA CGAGGAGGCG GGCAGCAGCT GCAGGCTGAC CTTGCAGCTT GGCGGA ATG        59
                                                              Met
                                                               1

GAC TGG CCT CAC AAC CTG CTG TTT CTT CTT ACC ATT TCC ATC TTC CTG         107
Asp Trp Pro His Asn Leu Leu Phe Leu Leu Thr Ile Ser Ile Phe Leu
         5                  10                  15

GGG CTG GGC CAG CCC AGG AGC CCC AAA AGC AAG AGG AAG GGG CAA GGG         155
Gly Leu Gly Gln Pro Arg Ser Pro Lys Ser Lys Arg Lys Gly Gln Gly
         20                  25                  30
```

-continued

```
CGG CCT GGG CCC CTG GCC CCT GGC CCT CAC CAG GTG CCA CTG GAC CTG      203
Arg Pro Gly Pro Leu Ala Pro Gly Pro His Gln Val Pro Leu Asp Leu
         35                  40                  45

GTG TCA CGG ATG AAA CCG TAT GCC CGC ATG GAG GAG TAT GAG AGG AAC      251
Val Ser Arg Met Lys Pro Tyr Ala Arg Met Glu Glu Tyr Glu Arg Asn
 50                  55                  60                  65

ATC GAG GAG ATG GTG GCC CAG CTG AGG AAC AGC TCA GAG CTG GCC CAG      299
Ile Glu Glu Met Val Ala Gln Leu Arg Asn Ser Ser Glu Leu Ala Gln
                     70                  75                  80

AGA AAG TGT GAG GTC AAC TTG CAG CTG TGG ATG TCC AAC AAG AGG AGC      347
Arg Lys Cys Glu Val Asn Leu Gln Leu Trp Met Ser Asn Lys Arg Ser
                         85                  90                  95

CTG TCT CCC TGG GGC TAC AGC ATC AAC CAC GAC CCC AGC CGT ATC CCC      395
Leu Ser Pro Trp Gly Tyr Ser Ile Asn His Asp Pro Ser Arg Ile Pro
                100                 105                 110

GTG GAC CTG CCG GAG GCA CGG TGC CTG TGT CTG GGC TGT GTG AAC CCC      443
Val Asp Leu Pro Glu Ala Arg Cys Leu Cys Leu Gly Cys Val Asn Pro
            115                 120                 125

TTC ACC ATG CAG GAG GAC CGC AGC ATG GTG AGC GTG CCG GTG TTC AGC      491
Phe Thr Met Gln Glu Asp Arg Ser Met Val Ser Val Pro Val Phe Ser
130                 135                 140                 145

CAG GTT CCT GTG CGC CGC CGC CTC TGC CCG CCA CCG CCC CGC ACA GGG      539
Gln Val Pro Val Arg Arg Arg Leu Cys Pro Pro Pro Pro Arg Thr Gly
                    150                 155                 160

CCT TGC CGC CAG CGC GCA GTC ATG GAG ACC ATC GCT GTG GGC TGC ACC      587
Pro Cys Arg Gln Arg Ala Val Met Glu Thr Ile Ala Val Gly Cys Thr
                        165                 170                 175

TGC ATC TTC TGAATCACCT GGCCCAGAAG CCAGGCCAGC AGCCCGAGAC CATCCTCCT    645
Cys Ile Phe
            180

TGCACCTTTG TGCCAAGAAA GGCCTATGAA AAGTAAACAC TGACTTTTGA AAGCCAGAAA    705

AAAAAAAAAA AAAAAAAATT CCTGCGGCCG C                                   736

(2) INFORMATION FOR SEQ ID NO: 2:

(i) SEQUENCE CHARACTERISTICS:
         (A) LENGTH: 180 amino acids
         (B) TYPE: amino acid
         (C) STRANDEDNESS: single
         (D) TOPOLOGY: linear (ii) MOLECULE TYPE: protein (v) FRAGMENT TYPE: internal (xi) SEQUENCE DESCRIPTION: SEQ ID NO: 2:

Met Asp Trp Pro His Asn Leu Leu Phe Leu Leu Thr Ile Ser Ile Phe
 1               5                  10                  15

Leu Gly Leu Gly Gln Pro Arg Ser Pro Lys Ser Lys Arg Lys Gly Gln
             20                  25                  30

Gly Arg Pro Gly Pro Leu Ala Pro Gly Pro His Gln Val Pro Leu Asp
         35                  40                  45

Leu Val Ser Arg Met Lys Pro Tyr Ala Arg Met Glu Glu Tyr Glu Arg
     50                  55                  60

Asn Ile Glu Glu Met Val Ala Gln Leu Arg Asn Ser Ser Glu Leu Ala
 65                  70                  75                  80

Gln Arg Lys Cys Glu Val Asn Leu Gln Leu Trp Met Ser Asn Lys Arg
                 85                  90                  95

Ser Leu Ser Pro Trp Gly Tyr Ser Ile Asn His Asp Pro Ser Arg Ile
            100                 105                 110
```

```
Pro Val Asp Leu Pro Glu Ala Arg Cys Leu Cys Leu Gly Cys Val Asn
        115                 120                 125

Pro Phe Thr Met Gln Glu Asp Arg Ser Met Val Ser Val Pro Val Phe
        130                 135                 140

Ser Gln Val Pro Val Arg Arg Arg Leu Cys Pro Pro Pro Arg Thr
145                 150                 155                 160

Gly Pro Cys Arg Gln Arg Ala Val Met Glu Thr Ile Ala Val Gly Cys
                165                 170                 175

Thr Cys Ile Phe
            180
```

(2) INFORMATION FOR SEQ ID NO: 3:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 3:

```
AGGCGGGCAN AGCTGCAGGC TGACCTTGCA GCTTGGCGGA ATGGACTGGC CTCACAACCT    60
GCTGTTTCTT CTTACCATTT CCATCTTCCT GGGGCTGGGC AGCCAGGAGC CCCAAAAGCA   120
AGAGGAAGGG GCAAGGGCGG CCTGGGCCCN TGGCCTGGCC TCACCAGGTG CCACTGGACC   180
TGGTGTCACG GATGAAACCG TATGCCCGCA TGGAGGAGTA TGAGAGGAAC ATCGAGGAGA   240
TGGTGGCCCA GCTGAGGAAC AGCTCANAAG CTGGCCCAGA GAAAGTGTGA GGTCAACTTG   300
CAGCTGTGGA TGTCCAACAA GAAGGAGCCT GTCTCCCTTG GGCTACAAG CATCAACCAC    360
CGACCCCAGC CGTATCCCCG TGGGACCTTG CCGGGAC                            397
```

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13265

(xi) SEQUENCE DESCRIPTION: SEQ ID NO: 4:

```
TTACCATTTC CATCTTCC                                                  18
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13266

(xi) SEQUENCE DESCRIPTION: SEQ ID NO: 5:

```
CCCTTCCTCT TGCTTTTG                                                  18
```

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13326

(xi) SEQUENCE DESCRIPTION: SEQ ID NO: 6:

CAAGGATCCC AGCCCAGGAG CCCCAAAAG                          29

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13330

(xi) SEQUENCE DESCRIPTION: SEQ ID NO: 7:

GACCTCGAGT CAGAAGATGC AGGTGCAGCC                        30

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13325

(xi) SEQUENCE DESCRIPTION: SEQ ID NO: 8:

GTCGAATTCA TGGACTGGCC TCACAACCTG                        30

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13327

(xi) SEQUENCE DESCRIPTION: SEQ ID NO: 9:

GAAGGATCCG AAGATGCAGG TGCAGCC                            27

(2) INFORMATION FOR SEQ ID NO: 10:

(i) SEQUENCE CHARACTERISTICS:
        (A) LENGTH: 10 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 10:

Asp Tyr Lys Asp Asp Asp Lys Gly Ser
1               5                  10

(2) INFORMATION FOR SEQ ID NO: 11:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 50...589
        (D) OTHER INFORMATION:

(xi) SEQUENCE DESCRIPTION: SEQ ID NO: 11:

```
GGGGTTCCTG GCGGGTGGCA GCTGCGGGCC TGCCGCCTGA CTTGGTGGG ATG GAC TGG      58
                                                       Met Asp Trp
                                                        1

CCG CAC AGC CTG CTC TTC CTC CTG GCC ATC TCC ATC TTC CTG GCG CCA       106
Pro His Ser Leu Leu Phe Leu Leu Ala Ile Ser Ile Phe Leu Ala Pro
     5              10                  15

AGC CAC CCC CGG AAC ACC AAA GGC AAA AGA AAA GGG CAA GGG AGG CCC       154
Ser His Pro Arg Asn Thr Lys Gly Lys Arg Lys Gly Gln Gly Arg Pro
 20              25                  30                  35

AGT CCC TTG GCC CCT GGG CCT CAT CAG GTG CCG CTG GAC CTG GTG TCT       202
Ser Pro Leu Ala Pro Gly Pro His Gln Val Pro Leu Asp Leu Val Ser
             40                  45                  50

CGA GTA AAG CCC TAC GCT CGA ATG GAA GAG TAT GAG CGG AAC CTT GGG       250
Arg Val Lys Pro Tyr Ala Arg Met Glu Glu Tyr Glu Arg Asn Leu Gly
             55                  60                  65

GAG ATG GTG GCC CAG CTG AGG AAC AGC TCC GAG CCA GCC AAG AAG AAA       298
Glu Met Val Ala Gln Leu Arg Asn Ser Ser Glu Pro Ala Lys Lys Lys
         70                  75                  80

TGT GAA GTC AAT CTA CAG CTG TGG TTG TCC AAC AAG AGG AGC CTG TCC       346
Cys Glu Val Asn Leu Gln Leu Trp Leu Ser Asn Lys Arg Ser Leu Ser
     85                  90                  95

CCA TGG GGC TAC AGC ATC AAC CAC GAC CCC AGC CGC ATC CCT GCG GAC       394
Pro Trp Gly Tyr Ser Ile Asn His Asp Pro Ser Arg Ile Pro Ala Asp
100             105                 110                 115

TTG CCC GAG GCG CGG TGC CTA TGT TTG GGT TGC GTG AAT CCC TTC ACC       442
Leu Pro Glu Ala Arg Cys Leu Cys Leu Gly Cys Val Asn Pro Phe Thr
             120                 125                 130

ATG CAG GAG GAC CGT AGC ATG GTG AGC GTG CCA GTG TTC AGC CAG GTG       490
Met Gln Glu Asp Arg Ser Met Val Ser Val Pro Val Phe Ser Gln Val
             135                 140                 145

CCG GTG CGC CGC CGC CTC TGT CCT CAA CCT CCT CGC CCT GGG CCC TGC       538
Pro Val Arg Arg Arg Leu Cys Pro Gln Pro Pro Arg Pro Gly Pro Cys
             150                 155                 160

CGC CAG CGT GTC GTC ATG GAG ACC ATC GCT GTG GGT TGC ACC TGC ATC       586
Arg Gln Arg Val Val Met Glu Thr Ile Ala Val Gly Cys Thr Cys Ile
         165                 170                 175

TTC TGAGCCAACC ACCAACCCGG TGGCCTCTGC AACAACCCTC CCTCCCTGCA CCCA       645
Phe
180
```

GTGACCCTCA AGGCTGATAA ACAGTAAACG CTGTTCTTTG TAAAGGA                    692

(2) INFORMATION FOR SEQ ID NO: 12:

(i) SEQUENCE CHARACTERISTICS:
        (A) LENGTH: 180 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 12:

```
Met Asp Trp Pro His Ser Leu Leu Phe Leu Leu Ala Ile Ser Ile Phe
 1               5                  10                  15

Leu Ala Pro Ser His Pro Arg Asn Thr Lys Gly Lys Arg Lys Gly Gln
            20                  25                  30

Gly Arg Pro Ser Pro Leu Ala Pro Gly Pro His Gln Val Pro Leu Asp
        35                  40                  45

Leu Val Ser Arg Val Lys Pro Tyr Ala Arg Met Glu Glu Tyr Glu Arg
    50                  55                  60

Asn Leu Gly Glu Met Val Ala Gln Leu Arg Asn Ser Ser Glu Pro Ala
65                  70                  75                  80

Lys Lys Lys Cys Glu Val Asn Leu Gln Leu Trp Leu Ser Asn Lys Arg
                85                  90                  95

Ser Leu Ser Pro Trp Gly Tyr Ser Ile Asn His Asp Pro Ser Arg Ile
            100                 105                 110

Pro Ala Asp Leu Pro Glu Ala Arg Cys Leu Cys Leu Gly Cys Val Asn
        115                 120                 125

Pro Phe Thr Met Gln Glu Asp Arg Ser Met Val Ser Val Pro Val Phe
    130                 135                 140

Ser Gln Val Pro Val Arg Arg Arg Leu Cys Pro Gln Pro Pro Arg Pro
145                 150                 155                 160

Gly Pro Cys Arg Gln Arg Val Val Met Glu Thr Ile Ala Val Gly Cys
                165                 170                 175

Thr Cys Ile Phe
            180
```

(2) INFORMATION FOR SEQ ID NO: 13:

(i) SEQUENCE CHARACTERISTICS:
        (A) LENGTH: 497 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGGGTTCCTG GCGGGTGGCA GCTGCGGGCC TGCCGCCTGA CTTGGTGGGA TGGACTGGCC    60

GCACAGCCTG CTCTTCCTCC TGGCCATCTC CATCTTCCTG GCGCCAAGCC ACCCCCGGAA    120

CACCAAAGGC AAAAGAAAAG GGCAAGGGAG GCCCAGTCCC TTGGCCCCTG GGCTCATCAG    180

GTGCCGCTGG ACCTGGTGTC TCGAGTAAAG CCCTACGCTC GAATGGAAGA GTATGAGCGG    240

AACCTTGGGG AGATGGTGGC CCAGCTGAGG AACAGCTCCG AGCCAGCCAA GAAGAAATGT    300

GAAGTCAATC TACAGCTGTG GTTGTCCAAC AAGAGGAGCC TGTCCCCATG GGGCTACAGC    360

ATCAACCACG ACCCCAGCCG CATCCCTGCG GACTTGCCCG AGGCGCGGTG CCTATGTTTG    420

```
GGTTGCGTGA ATCCCTTCAC CATGCAGGAG GACCGTAGCA TGGTGAGCGT GCCAGTGTTC        480

AGCCAGGTGC CGGTGCG                                                      497
```

(2) INFORMATION FOR SEQ ID NO: 14:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

```
Gln Pro Arg Ser Pro Lys Ser Lys Arg Lys Gly Gln Gly Arg Pro Gly
 1               5                  10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
            130                 135                 140

Gln Arg Ala Val Met Glu Thr Ile Ala Val Gly Cys Thr Cys Ile Phe
145                 150                 155                 160
```

(2) INFORMATION FOR SEQ ID NO: 15:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

```
Gln Pro Arg Ala Pro Lys Ser Lys Arg Lys Gly Gln Gly Arg Pro Gly
 1               5                  10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
        35                  40                  45

Met Val Ala Gln Leu Arg Asn Ser Ser Glu Leu Ala Gln Arg Lys Cys
    50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95
```

```
Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130             135                 140

Gln Arg Ala Val Met Glu Thr Ile Ala Val Gly Cys Thr Cys Ile Phe
145                 150                 155                 160

(2) INFORMATION FOR SEQ ID NO: 16:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Gln Pro Arg Ser Pro Lys Ala Lys Arg Lys Gly Gln Gly Arg Pro Gly
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130             135                 140

Gln Arg Ala Val Met Glu Thr Ile Ala Val Gly Cys Thr Cys Ile Phe
145                 150                 155                 160

(2) INFORMATION FOR SEQ ID NO: 17:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

Gln Pro Arg Ser Pro Lys Ser Lys Arg Lys Gly Gln Gly Arg Pro Ala
1               5                   10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
50                  55                  60
```

```
Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
                 85                  90                  95

Pro Glu Ala Arg Cys Leu Cys Leu Gly Cys Val Asn Pro Phe Thr Met
                100                 105                 110

Gln Glu Asp Arg Ser Met Val Ser Val Pro Val Phe Ser Gln Val Pro
                115                 120                 125

Val Arg Arg Leu Cys Pro Pro Pro Arg Thr Gly Pro Cys Arg
    130                 135                 140

Gln Arg Ala Val Met Glu Thr Ile Ala Val Gly Cys Thr Cys Ile Phe
145                 150                 155                 160
```

(2) INFORMATION FOR SEQ ID NO: 18:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Gln Pro Arg Ser Pro Lys Ser Lys Arg Lys Gly Gln Gly Arg Pro Gly
  1               5                  10                  15

Pro Leu Ala Pro Gly Pro His Gln Val Pro Leu Asp Leu Val Ala Arg
                 20                  25                  30

Met Lys Pro Tyr Ala Arg Met Glu Glu Tyr Glu Arg Asn Ile Glu Glu
             35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
                 85                  90                  95

Pro Glu Ala Arg Cys Leu Cys Leu Gly Cys Val Asn Pro Phe Thr Met
                100                 105                 110

Gln Glu Asp Arg Ser Met Val Ser Val Pro Val Phe Ser Gln Val Pro
                115                 120                 125

Val Arg Arg Leu Cys Pro Pro Pro Arg Thr Gly Pro Cys Arg
    130                 135                 140

Gln Arg Ala Val Met Glu Thr Ile Ala Val Gly Cys Thr Cys Ile Phe
145                 150                 155                 160
```

(2) INFORMATION FOR SEQ ID NO: 19:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Gln Pro Arg Ser Pro Lys Ser Lys Arg Lys Gly Gln Gly Arg Pro Gly
  1               5                  10                  15

Pro Leu Ala Pro Gly Pro His Gln Val Pro Leu Asp Leu Val Ser Arg
```

```
              20                  25                  30
Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
            130                 135                 140

Gln Arg Val Val Met Glu Thr Ile Ala Val Gly Cys Thr Cys Ile Phe
145                 150                 155                 160

(2) INFORMATION FOR SEQ ID NO: 20:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Gln Pro Arg Ser Pro Lys Ser Lys Arg Lys Gly Gln Gly Arg Pro Gly
 1               5                  10                  15

Pro Leu Ala Pro Gly Pro His Gln Val Pro Leu Asp Leu Val Ser Arg
            20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
            130                 135                 140

Gln Arg Leu Val Met Glu Thr Ile Ala Val Gly Cys Thr Cys Ile Phe
145                 150                 155                 160

(2) INFORMATION FOR SEQ ID NO: 21:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO: 21:

```
Gln Pro Arg Ser Pro Lys Ser Lys Arg Lys Gly Gln Gly Arg Pro Gly
  1               5                  10                  15

Pro Leu Ala Pro Gly Pro His Gln Val Pro Leu Asp Leu Val Ser Arg
             20                  25                  30

Met Lys Pro Tyr Ala Arg Met Glu Glu Tyr Glu Arg Asn Ile Glu Glu
             35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
             85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130                 135                 140

Gln Arg Phe Val Met Glu Thr Ile Ala Val Gly Cys Thr Cys Ile Phe
145                 150                 155                 160
```

(2) INFORMATION FOR SEQ ID NO: 22:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

```
Gln Pro Arg Ser Pro Lys Ser Lys Arg Lys Gly Gln Gly Arg Pro Gly
  1               5                  10                  15

Pro Leu Ala Pro Gly Pro His Gln Val Pro Leu Asp Leu Val Gly Arg
             20                  25                  30

Met Lys Pro Tyr Ala Arg Met Glu Glu Tyr Glu Arg Asn Ile Glu Glu
             35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
             85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130                 135                 140

Gln Arg Ala Val Met Glu Thr Ile Ala Val Gly Cys Thr Cys Ile Phe
145                 150                 155                 160
```

(2) INFORMATION FOR SEQ ID NO: 23:

(i) SEQUENCE CHARACTERISTICS:
    (A) LENGTH: 160 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 23:

```
Gln Pro Arg Ser Pro Lys Ser Lys Arg Lys Gly Gln Gly Arg Pro Ser
 1               5                  10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
               100                 105                 110

Gln Glu Asp Arg Ser Met Val Ser Val Pro Val Phe Ser Gln Val Pro
           115                 120                 125

Val Arg Arg Arg Leu Cys Pro Pro Pro Arg Thr Gly Pro Cys Arg
130                 135                 140

Gln Arg Ala Val Met Glu Thr Ile Ala Val Gly Cys Thr Cys Ile Phe
145                 150                 155                 160
```

(2) INFORMATION FOR SEQ ID NO: 24:

(i) SEQUENCE CHARACTERISTICS:
    (A) LENGTH: 160 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 24:

```
Gln Pro Arg Ser Pro Lys Val Lys Arg Lys Gly Gln Gly Arg Pro Gly
 1               5                  10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
 50                  55                  60

Glu Val Asn Leu Gln Leu Trp Met Ser Asn Lys Arg Ser Leu Ser Pro
 65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
               100                 105                 110

Gln Glu Asp Arg Ser Met Val Ser Val Pro Val Phe Ser Gln Val Pro
           115                 120                 125

Val Arg Arg Arg Leu Cys Pro Pro Pro Arg Thr Gly Pro Cys Arg
130                 135                 140
```

Gln Arg Ala Val Met Glu Thr Ile Ala Val Gly Cys Thr Cys Ile Phe
145                 150                 155                 160

(2) INFORMATION FOR SEQ ID NO: 25:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

Gln Pro Arg Val Pro Lys Ser Lys Arg Lys Gly Gln Gly Arg Pro Gly
1                   5                   10                  15

Pro Leu Ala Pro Gly Pro His Gln Val Pro Leu Asp Leu Val Ser Arg
                20                  25                  30

Met Lys Pro Tyr Ala Arg Met Glu Glu Tyr Glu Arg Asn Ile Glu Glu
            35                  40                  45

Met Val Ala Gln Leu Arg Asn Ser Ser Glu Leu Ala Gln Arg Lys Cys
50                  55                  60

Glu Val Asn Leu Gln Leu Trp Met Ser Asn Lys Arg Ser Leu Ser Pro
65                  70                  75                  80

Trp Gly Tyr Ser Ile Asn His Asp Pro Ser Arg Ile Pro Val Asp Leu
                85                  90                  95

Pro Glu Ala Arg Cys Leu Cys Leu Gly Cys Val Asn Pro Phe Thr Met
            100                 105                 110

Gln Glu Asp Arg Ser Met Val Ser Val Pro Val Phe Ser Gln Val Pro
            115                 120                 125

Val Arg Arg Arg Leu Cys Pro Pro Pro Arg Thr Gly Pro Cys Arg
130                 135                 140

Gln Arg Ala Val Met Glu Thr Ile Ala Val Gly Cys Thr Cys Ile Phe
145                 150                 155                 160

(2) INFORMATION FOR SEQ ID NO: 26:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Cys Glu Val Asn Leu Gln Leu Trp Met Ser Asn Lys Arg Ser Leu Ser
1                   5                   10                  15

Pro Trp Gly Tyr Ser Ile Asn His Asp Pro Ser Arg Ile Pro Val Asp
                20                  25                  30

Leu Pro Glu Ala Arg Cys Leu Cys Leu Gly Cys Val Asn Pro Phe Thr
            35                  40                  45

Met Gln Glu Asp Arg Ser Met Val Ser Val Pro Val Phe Ser Gln Val
50                  55                  60

Pro Val Arg Arg Arg Leu Cys Pro Pro Pro Arg Thr Gly Pro Cys
65                  70                  75                  80

Arg Gln Arg Ala Val Met Glu Thr Ile Ala Val Gly Cys Thr Cys Ile
                85                  90                  95

Phe (2) INFORMATION FOR SEQ ID NO: 27:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Pro Arg Ser Pro Lys Ser Lys Arg Lys Gly Gln Gly Arg Pro Gly Pro
1               5                   10                  15

Leu Ala Pro Gly Pro His Gln Val Pro Leu Asp Leu Val Ser Arg Met
                20                  25                  30

Lys Pro Tyr Ala Arg Met Glu Glu Tyr Glu Arg Asn Ile Glu Glu Met
            35                  40                  45

Val Ala Gln Leu Arg Asn Ser Ser Glu Leu Ala Gln Arg Lys Cys Glu
50                  55                  60

Val Asn Leu Gln Leu Trp Met Ser Asn Lys Arg Ser Leu Ser Pro Trp
65                  70                  75                  80

Gly Tyr Ser Ile Asn His Asp Pro Ser Arg Ile Pro Val Asp Leu Pro
                85                  90                  95

Glu Ala Arg Cys
            100

(2) INFORMATION FOR SEQ ID NO: 28:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Pro Arg Ser Pro Lys Ser Lys Arg Lys Gly Gln Gly Arg Pro Gly Pro
1               5                   10                  15

Leu (2) INFORMATION FOR SEQ ID NO: 29:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Arg Met Lys Pro Tyr Ala Arg Met Glu Glu Tyr Glu Arg Asn Ile Glu
1               5                   10                  15

Glu (2) INFORMATION FOR SEQ ID NO: 30:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Asn His Asp Pro Ser Arg Ile Pro Val Asp Leu Pro Glu Ala Arg Cys
1               5                   10                  15

(2) INFORMATION FOR SEQ ID NO: 31:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Pro Val Arg Arg Arg Leu Cys Pro Pro Pro Arg Thr Gly Pro Cys
1               5                   10                  15

Arg Gln Arg (2) INFORMATION FOR SEQ ID NO: 32:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Pro Arg Ser Pro Lys Ser Lys Arg Lys Gly Gln Gly Arg Pro Gly Pro
1               5                   10                  15

Leu Ala Pro Gly Pro His Gln Val Pro Leu Asp Leu Val Ser Arg Met
            20                  25                  30

Lys Pro Tyr Ala Arg Met Glu Glu Tyr Glu Arg Asn Ile Glu Glu
        35                  40                  45

(2) INFORMATION FOR SEQ ID NO: 33:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Arg Met Lys Pro Tyr Ala Arg Met Glu Glu Tyr Glu Arg Asn Ile Glu
1               5                   10                  15

Glu Met Val Ala Gln Leu Arg Asn Ser Ser Glu Leu Ala Gln Arg Lys
            20                  25                  30

Cys Glu Val Asn Leu Gln Leu Trp Met Ser Asn Lys Arg Ser Leu Ser
            35                  40                  45

Pro Trp Gly Tyr Ser Ile Asn His Asp Pro Ser Arg Ile Pro Val Asp
        50                  55                  60

Leu Pro Glu Ala Arg Cys
65                  70

(2) INFORMATION FOR SEQ ID NO: 34:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Asn His Asp Pro Ser Arg Ile Pro Val Asp Leu Pro Glu Ala Arg Cys
 1               5                  10                  15

Leu Cys Leu Gly Cys Val Asn Pro Phe Thr Met Gln Glu Asp Arg Ser
            20                  25                  30

Met Val Ser Val Pro Val Phe Ser Gln Val Pro Val Arg Arg Arg Leu
        35                  40                  45

Cys Pro Pro Pro Arg Thr Gly Pro Cys Arg Gln Arg
    50                  55                  60

(2) INFORMATION FOR SEQ ID NO: 35:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Asn His Asp Pro Ser Arg Ile Pro Val Asp Leu Pro Glu Ala Arg Cys
 1               5                  10                  15

Leu Cys Leu Gly Cys Val Asn Pro Phe Thr Met Gln Glu Asp Arg Ser
            20                  25                  30

Met Val Ser Val Pro Val Phe Ser Gln Val Pro Val Arg Arg Arg Leu
        35                  40                  45

Cys Pro Pro Pro Arg Thr Gly Pro Cys Arg Gln Arg Ala Val Met
    50                  55                  60

Glu Thr Ile Ala Val Gly Cys Thr Cys
65                  70

(2) INFORMATION FOR SEQ ID NO: 36:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

Arg Ser Pro Lys Ser Lys Arg Lys Gly Gln Gly Arg Pro Gly Pro Leu
 1               5                  10                  15

Ala Pro Gly Pro His Gln Val Pro Leu Asp Leu Val Ser Arg Met Lys
            20                  25                  30

Pro Tyr Ala Arg Met Glu Glu Tyr Glu Arg Asn Ile Glu Glu Met Val
        35                  40                  45

Ala Gln Leu Arg Asn Ser Ser Glu Leu Ala Gln Arg Lys Cys Glu Val
    50                  55                  60

Asn Leu Gln Leu Trp Met Ser Asn Lys Arg Ser Leu Ser Pro Trp Gly
65                  70                  75                  80

Tyr Ser Ile Asn His Asp Pro Ser Arg Ile Pro Val Asp Leu Pro Glu

-continued

```
                    85                  90                  95
Ala Arg Cys Leu Cys Leu Gly Cys Val Asn Pro Phe Thr Met Gln Glu
                100                 105                 110
Asp Arg Ser Met Val Ser Val Pro Val Phe Ser Gln Val Pro Val Arg
            115                 120                 125
Arg Arg Leu Cys Pro Pro Pro Arg Thr Gly Pro Cys Arg Gln Arg
        130                 135                 140
Ala Val Met Glu Thr Ile Ala Val Gly Cys Thr Cys Ile Phe
145                 150                 155
```

(2) INFORMATION FOR SEQ ID NO: 37:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

```
Ser Lys Arg Lys Gly Gln Gly Arg Pro Gly Pro Leu Ala Pro Gly Pro
1               5                   10                  15
His Gln Val Pro Leu Asp Leu Val Ser Arg Met Lys Pro Tyr Ala Arg
            20                  25                  30
Met Glu Glu Tyr Glu Arg Asn Ile Glu Glu Met Val Ala Gln Leu Arg
        35                  40                  45
Asn Ser Ser Glu Leu Ala Gln Arg Lys Cys Glu Val Asn Leu Gln Leu
    50                  55                  60
Trp Met Ser Asn Lys Arg Ser Leu Ser Pro Trp Gly Tyr Ser Ile Asn
65                  70                  75                  80
His Asp Pro Ser Arg Ile Pro Val Asp Leu Pro Glu Ala Arg Cys Leu
                85                  90                  95
Cys Leu Gly Cys Val Asn Pro Phe Thr Met Gln Glu Asp Arg Ser Met
                100                 105                 110
Val Ser Val Pro Val Phe Ser Gln Val Pro Val Arg Arg Arg Leu Cys
            115                 120                 125
Pro Pro Pro Arg Thr Gly Pro Cys Arg Gln Arg Ala Val Met Glu
        130                 135                 140
Thr Ile Ala Val Gly Cys Thr Cys Ile Phe
145                 150
```

(2) INFORMATION FOR SEQ ID NO: 38:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 38:

```
Lys Gly Gln Gly Arg Pro Gly Pro Leu Ala Pro Gly Pro His Gln Val
1               5                   10                  15
Pro Leu Asp Leu Val Ser Arg Met Lys Pro Tyr Ala Arg Met Glu Glu
            20                  25                  30
Tyr Glu Arg Asn Ile Glu Glu Met Val Ala Gln Leu Arg Asn Ser Ser
        35                  40                  45
```

```
Glu Leu Ala Gln Arg Lys Cys Glu Val Asn Leu Gln Leu Trp Met Ser
 50                  55                  60

Asn Lys Arg Ser Leu Ser Pro Trp Gly Tyr Ser Ile Asn His Asp Pro
 65                  70                  75                  80

Ser Arg Ile Pro Val Asp Leu Pro Glu Ala Arg Cys Leu Cys Leu Gly
                 85                  90                  95

Cys Val Asn Pro Phe Thr Met Gln Glu Asp Arg Ser Met Val Ser Val
                100                 105                 110

Pro Val Phe Ser Gln Val Pro Val Arg Arg Arg Leu Cys Pro Pro Pro
                115                 120                 125

Pro Arg Thr Gly Pro Cys Arg Gln Arg Ala Val Met Glu Thr Ile Ala
                130                 135                 140

Val Gly Cys Thr Cys Ile Phe
145                 150

(2) INFORMATION FOR SEQ ID NO: 39:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 39:

His Pro Arg Asn Thr Lys Gly Lys Arg Lys Gly Gln Gly Arg Pro Ser
 1               5                  10                  15

Pro Leu Ala Pro Gly Pro His Gln Val Pro Leu Asp Leu Val Ser Arg
                 20                  25                  30

Val Lys Pro Tyr Ala Arg Met Glu Glu Tyr Glu Arg Asn Leu Gly Glu
                 35                  40                  45

Met Val Ala Gln Leu Arg Asn Ser Ser Glu Pro Ala Lys Lys Lys Cys
 50                  55                  60

Glu Val Asn Leu Gln Leu Trp Leu Ser Asn Lys Arg Ser Leu Ser Pro
 65                  70                  75                  80

Trp Gly Tyr Ser Ile Asn His Asp Pro Ser Arg Ile Pro Ala Asp Leu
                 85                  90                  95

Pro Glu Ala Arg Cys Leu Cys Leu Gly Cys Val Asn Pro Phe Thr Met
                100                 105                 110

Gln Glu Asp Arg Ser Met Val Ser Val Pro Val Phe Ser Gln Val Pro
                115                 120                 125

Val Arg Arg Arg Leu Cys Pro Gln Pro Pro Arg Pro Gly Pro Cys Arg
                130                 135                 140

Gln Arg Val Val Met Glu Thr Ile Ala Val Gly Cys Thr Cys Ile Phe
145                 150                 155                 160

(2) INFORMATION FOR SEQ ID NO: 40:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 40:

Arg Asn Thr Lys Gly Lys Arg Lys Gly Gln Gly Arg Pro Ser Pro Leu
 1               5                  10                  15
```

```
Ala Pro Gly Pro His Gln Val Pro Leu Asp Leu Val Ser Arg Val Lys
            20                  25                  30

Pro Tyr Ala Arg Met Glu Glu Tyr Glu Arg Asn Leu Gly Glu Met Val
        35                  40                  45

Ala Gln Leu Arg Asn Ser Ser Glu Pro Ala Lys Lys Lys Cys Glu Val
    50                  55                  60

Asn Leu Gln Leu Trp Leu Ser Asn Lys Arg Ser Leu Ser Pro Trp Gly
65                  70                  75                  80

Tyr Ser Ile Asn His Asp Pro Ser Arg Ile Pro Ala Asp Leu Pro Glu
                85                  90                  95

Ala Arg Cys Leu Cys Leu Gly Cys Val Asn Pro Phe Thr Met Gln Glu
            100                 105                 110

Asp Arg Ser Met Val Ser Val Pro Val Phe Ser Gln Val Pro Val Arg
            115                 120                 125

Arg Arg Leu Cys Pro Gln Pro Arg Pro Gly Pro Cys Arg Gln Arg
    130                 135                 140

Val Val Met Glu Thr Ile Ala Val Gly Cys Thr Cys Ile Phe
145                 150                 155

(2) INFORMATION FOR SEQ ID NO: 41:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 41:

Lys Arg Lys Gly Gln Gly Arg Pro Gly Pro Leu Ala Pro Gly Pro His
1               5                   10                  15

Gln Val Pro Leu Asp Leu Val Ser Arg Met Lys Pro Tyr Ala Arg Met
            20                  25                  30

Glu Glu Tyr Glu Arg Asn Ile Glu Met Val Ala Gln Leu Arg Asn
        35                  40                  45

Ser Ser Glu Leu Ala Gln Arg Lys Cys Glu Val Asn Leu Gln Leu Trp
    50                  55                  60

Met Ser Asn Lys Arg Ser Leu Ser Pro Trp Gly Tyr Ser Ile Asn His
65                  70                  75                  80

Asp Pro Ser Arg Ile Pro Val Asp Leu Pro Glu Ala Arg Cys Leu Cys
                85                  90                  95

Leu Gly Cys Val Asn Pro Phe Thr Met Gln Glu Asp Arg Ser Met Val
            100                 105                 110

Ser Val Pro Val Phe Ser Gln Val Pro Val Arg Arg Arg Leu Cys Pro
            115                 120                 125

Pro Pro Pro Arg Thr Gly Pro Cys Arg Gln Arg Ala Val Met Glu Thr
    130                 135                 140

Ile Ala Val Gly Cys Thr Cys Ile Phe
145                 150

(2) INFORMATION FOR SEQ ID NO: 42:

(i) SEQUENCE CHARACTERISTICS:
        (A) LENGTH: 128 amino acids
        (B) TYPE: amino acid
        (C) STRANDEDNESS: single
        (D) TOPOLOGY: linear
```

(ii) MOLECULE TYPE: protein (xi) SEQUENCE DESCRIPTION: SEQ ID NO: 42:

```
Met Lys Pro Tyr Ala Arg Met Glu Glu Tyr Glu Arg Asn Ile Glu Glu
 1               5                  10                  15
Met Val Ala Gln Leu Arg Asn Ser Ser Glu Leu Ala Gln Arg Lys Cys
                20                  25                  30
Glu Val Asn Leu Gln Leu Trp Met Ser Asn Lys Arg Ser Leu Ser Pro
                35                  40                  45
Trp Gly Tyr Ser Ile Asn His Asp Pro Ser Arg Ile Pro Val Asp Leu
        50                  55                  60
Pro Glu Ala Arg Cys Leu Cys Leu Gly Cys Val Asn Pro Phe Thr Met
65                  70                  75                  80
Gln Glu Asp Arg Ser Met Val Ser Val Pro Val Phe Ser Gln Val Pro
                85                  90                  95
Val Arg Arg Arg Leu Cys Pro Pro Pro Arg Thr Gly Pro Cys Arg
                100                 105                 110
Gln Arg Ala Val Met Glu Thr Ile Ala Val Gly Cys Thr Cys Ile Phe
            115                 120                 125
```

(2) INFORMATION FOR SEQ ID NO: 43:

(i) SEQUENCE CHARACTERISTICS:
       (A) LENGTH: 157 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 43:

```
Arg Ser Pro Lys Ser Lys Arg Lys Gly Gln Gly Arg Pro Gly Pro Leu
 1               5                  10                  15
Ala Pro Gly Pro His Gln Val Pro Leu Asp Leu Val Ser Arg Met Lys
                20                  25                  30
Pro Tyr Ala Arg Met Glu Glu Tyr Glu Arg Asn Ile Glu Glu Met Val
                35                  40                  45
Ala Gln Leu Arg Asn Ser Ser Glu Leu Ala Gln Arg Lys Cys Glu Val
        50                  55                  60
Asn Leu Gln Leu Trp Met Ser Asn Lys Arg Ser Leu Ser Pro Trp Gly
65                  70                  75                  80
Tyr Ser Ile Asn His Asp Pro Ser Arg Ile Pro Val Asp Leu Pro Glu
                85                  90                  95
Ala Arg Cys Leu Cys Leu Gly Cys Val Asn Pro Phe Thr Met Gln Glu
                100                 105                 110
Asp Arg Ser Met Val Ser Val Pro Val Phe Ser Gln Val Pro Val Arg
            115                 120                 125
Arg Arg Leu Cys Pro Pro Pro Arg Thr Gly Pro Cys Arg Gln Arg
        130                 135                 140
Ala Val Met Glu Thr Ile Ala Val Gly Cys Thr Cys Ile
145                 150                 155
```

US 6,500,928 B1

MAMMALIAN CYTOKINE-LIKE FACTOR 7

This application is a continuation of U.S. application Ser. No. 09/066,745, filed Apr. 24, 1998, now abandoned which claims the benefit of U.S. Provisional Application Ser. No. 60/071,676 filed Jan. 16, 1998; and U.S. Provisional Application Ser. No. 60/044,886 filed Apr. 25, 1997.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair and regenerate damaged tissue. Examples of hormones and growth factors include the steroid hormones (e.g. estrogen, testosterone), parathyroid hormone, follicle stimulating hormone, the interleukins, Platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to proteins. Proteins may be integral membrane proteins that are linked to signaling pathways within the cell, such as second messenger systems. Other classes of proteins are soluble molecules, such as the transcription factors.

Of particular interest are cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia or receiving chemotherapy for cancer. The demonstrated in vivo activities of these cytokines illustrates the enormous clinical potential of, and need for, other cytokines, cytokine agonists, and cytokine antagonists.

SUMMARY OF THE INVENTION

The present invention addresses this need by providing a novel polypeptide called cytokine-like factor 7, hereinafter referred to as Zcyto7 and related compositions and methods.

Thus, one aspect of the present invention provides for an isolated Zcyto7 polypeptide having amino acid sequences as follows. Both the human and the mouse cDNAs have been discovered. The human sequences are defined by SEQ ID NOs: 1 and 2. The murine nucleotide and amino acid sequences are defined by SEQ ID NOs: 11 and 12.

The nucleotide sequence of SEQ ID NO:1 contains an open reading frame encoding a polypeptide of about 180 amino acids with the initial Met as shown in SEQ ID NO:1 and SEQ ID NO:2. A predicted signal sequence is comprised of amino acid residues 1–20, and the resultant predicted mature Zcyto7 polypeptide is represented by the amino acid sequence extending from amino acid residue 21, a glutamine to and including amino acid residue 180 a phenylalanine, also represented by SEQ ID NO: 14. Peptide mapping data indicate that mature Zcyto7 can be comprised of a number of N-terminal mature variants including the amino acid sequence extending from amino acid residue 23, an arginine to and including amino acid residue 180 of SEQ ID NO: 2, also defined by SEQ ID NO: 36; amino acid sequence extending from amino acid residue 27, a serine to and including amino acid residue 180 of SEQ ID NO: 2, also defined by SEQ ID NO: 37; the amino acid sequence defined by amino acid residue 30, a lysine, to and including amino acid residue 180 of SEQ ID NO: 2, also defined by SEQ ID NO: 38; amino acid sequence extending from amino acid 28, a lysine, to and including amino acid residue 180 of SEQ ID NO:2, also defined by SEQ ID NO: 41 and the amino acid sequence extending from amino acid residue 53, a methionine, to and including amino acid residue 180, also defined by SEQ ID NO: 42. The only observed cleavage at the carboxyl terminus is the phenylalanine at position 180 can be cleaved off. This can occur in all of the above-defined mature Zcyto7 polypeptides an example of which is shown by SEQ ID NO:43. Additional variants of human Zcyto7 are defined by SEQ ID NOs: 15–25. Within an additional embodiment, the polypeptide further comprises an affinity tag.

SEQ ID NOs: 11 and 12 define murine Zcyto7 wherein the mature protein extends from amino acid residues amino acid residue 21, a histidine, to and including amino acid residue 180 a phenylalanine, also defined by SEQ ID NO: 39; or as an alternative splice site from amino acid residue 23, an arginine, to and including amino acid 180 also defined by SEQ ID NO: 40. The present invention is also comprised of polypeptides having an amino acid sequence at least 90% identical, more preferably 95%, 97% or 99% identical to those Zcyto7 polypeptides defined in above.

An additional embodiment of the present invention relates to a peptide or polypeptide which has the amino acid sequence of an epitope-bearing portion of a Zcyto7 polypeptide having an amino acid sequence described above. Peptides or polypeptides having the amino acid sequence of an epitope-bearing portion of a Zcyto7 polypeptide of the present invention include portions of such polypeptides with at least nine, preferably at least 15 and more preferably at least 30 to 50 amino acids, although epitope-bearing polypeptides of any length up to and including the entire amino acid sequence of a polypeptide of the present invention described above are also included in the present invention. Examples of said polypeptides are defined by the amino acid sequences of SEQ ID NOs: 25–35. Also claimed are any of these polypeptides that are fused to another polypeptide or carrier molecule.

The present invention further comprises a polypeptide defined by SEQ ID NOs: 15–25 wherein the amino termini of said polypeptides are modified and begin at either amino acid residue 3, an arginine; amino acid residue 7, a serine; amino acid residue 8, a lysine; amino acid residue 10, a lysine or amino acid residue 33 methionine.

The present invention is further comprised of a polypeptide wherein the polypeptide is a polypeptide defined by SEQ ID NOs: 2, 12, 14–25 and 36 to 42 wherein the amino acid sequences end at the isoleucines at amino acid residue 179 of SEQ ID NO: 2, at amino acid residue 159 of SEQ ID NOs: 14–25, which corresponds to amino acid residue 157 of SEQ ID NO:36, amino acid residue 153 of SEQ ID NO:37, amino acid residue 150 of SEQ ID NO:38, amino acid residue 159 of SEQ ID NO: 39, amino acid residue 157 of SEQ ID NO:40, amino acid residue 152 SEQ ID NO:42, amino acid residue 127 of SEQ ID NO:42.

The present invention is further comprised of an isolated peptide or polypeptide of the above-described peptides or polypeptide having an amino acid sequence modified by addition, deletion and/or replacement of one or more amino acid residues and which maintains the biological activity of said peptide or polypeptide.

Within a further aspect of the invention there is provided a chimeric polypeptide consisting essentially of a first portion and a second portion joined by a peptide bond. The first portion of the chimeric polypeptide consists essentially of (a) a Zcyto7 polypeptide as described above (b) allelic variants of the polypeptides described above. The second portion of the chimeric polypeptide consists essentially of another polypeptide such as an affinity tag. Within one embodiment the affinity tag is an immunoglobulin $F_C$ polypeptide. The invention also provides expression vectors encoding the chimeric polypeptides and host cells transfected to produce the chimeric polypeptides.

Another aspect of the present invention provides for isolated nucleic acid molecules comprising a polynucleotide selected from the group consisting of: (a) a nucleotide sequence encoding the Zcyto7 polypeptides described above; (b) a nucleotide sequence encoding the polypeptides of SEQ ID NOs: 14–40 and (c) a nucleotide sequence complementary to any of to any of the nucleotide sequences in (a) or (b).

Further embodiments of the invention include isolated nucleic acid molecules that comprise a polynucleotide having a nucleotide sequence at least 90% identical, and more preferably 95%, 97%, 98% or 99% identical to any of the nucleotide sequences in (a), (b) or (c) above, or a polynucleotide which hybridizes under stringent hybridization conditions to a polynucleotide having a nucleotide sequence of (a) (b) or (c) above. An additional nucleic acid embodiment of the present invention relates to an isolated nucleic acid molecule comprising an amino acid of an epitope-bearing portion of a Zcyto7 polypeptide.

Within another aspect of the invention there is provided an expression vector comprising (a) a transcription promoter; (b) a DNA segment encoding a polypeptide described above, and (c) a transcription terminator, wherein the promoter, DNA segment, and terminator are operably linked.

Within a third aspect of the invention there is provided a cultured eukaryotic cell into which has been introduced an expression vector as disclosed above, wherein said cell expresses a protein polypeptide encoded by the DNA segment.

In another embodiment of the present invention is an isolated antibody that binds specifically to a Zcyto7 polypeptide described above. Also claimed is a method for producing antibodies which bind to a Zcyto7 polypeptide comprising inoculating a mammal with a Zcyto7 polypeptide or Zcyto7 epitope-bearing polypeptide so that the mammal produces antibodies to the polypeptide; and isolating said antibodies.

These and other aspects of the invention will become evident upon reference to the following detailed description.

DETAILED DESCRIPTION OF THE INVENTION

The teachings of all of the references cited herein are incorporated in their entirety herein by reference.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A [Nilsson et al, *EMBO J.* 4:1075 (1985); Nilsson et al., Methods Enzymol. 198:3 (1991)], glutathione S transferase [Smith and Johnson, Gene 20 67:31 (1988)], Glu-Glu affinity tag [Grussenmeyer et al., Proc. Natl. Acad. Sci. USA 82:7952–4 (1985)], substance P, FLAG™ peptide (Hopp et al., Biotechnology 6:1204–10 (1988), streptavidin binding peptide, or other antigenic epitope or binding domain. See, in general, Ford et al., Protein Expression and Purification 2: 95–107 (1991). DNAs encoding affinity tags are available from Commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence The term allelic variant is also used herein to denote a protein encoded by an allelic variant of a gene.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art. See for example, Dynan and Tijan, Nature 316:774–78 (1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

A "soluble protein" is a protein polypeptide that is not bound to a cell membrane.

Within preferred embodiments of the invention the isolated polynucleotides will hybridize to similar sized regions of the DNA of SEQ ID NO: 1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is about 0.02 M or less at pH 7 and the temperature is at least about 60° C. As previously noted, the isolated polynucleotides of the present invention include DNA and RNA. Methods for isolating DNA and RNA are well known in the art. Total RNA can be prepared using guanidine HCl extraction followed by isolation by centrifugation in a CsCl gradient [Chirgwin et al., Biochemistry 18:52–94 (1979)]. Poly (A)$^+$ RNA is prepared from total RNA using the method of Aviv and Leder, Proc. Natl. Acad. Sci. USA 69:1408–1412 (1972). Complementary DNA (cDNA) is prepared from poly(A)$^+$ RNA using known methods. Polynucleotides encoding Zcyto7 polypeptides are then identified and isolated by, for example, hybridization or PCR.

Additionally, the polynucleotides of the present invention can be synthesized using a DNA synthesizer. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. In addition to the protein coding sequence, synthetic genes can be designed with terminal sequences that facilitate insertion into a restriction endonuclease sites of a cloning vector and other sequences should also be added that contain signals for the proper initiation and termination of transcription and translation.

See Glick, Bernard R. and Jack J. Pasternak, Molecular Biotechnology, Principles & Applications of Recombinant DNA (ASM Press, Washington, D.C. 1994), Itakura, K. et al. Synthesis and use of synthetic oligonucleotides. Annu. Rev. Biochem. 53: 323–356 (1984), and Climie, S. et al. Chemical synthesis of the thymidylate synthase gene. Proc. Natl. Acad. Sci. USA 87:633–637 (1990).

Those skilled in the art will recognize that the sequences disclosed in SEQ ID NOS:1 and 2 represent a single allele of the human. There are a number of naturally occurring mature N-terminal variants having the leader sequence cleaved at differing positions. They include the sequences defined by SEQ ID NOs 14, 36, 37 and 38. Allelic variants of these sequences can be cloned by probing cDNA or genomic libraries from different individuals according to standard procedures. Examples of variants of human Zcyto7 are represented by the polypeptides of SEQ ID NOs: 15–25.

The murine Zcyto7 cDNA and protein are disclosed by SEQ ID NOs: 11 and 12. The mature Zcyto7 polypeptide is defined by SEQ ID NOs: 39 and 40.

The present invention further provides counterpart proteins and polynucleotides from other species ("species orthologs"). Of particular interest are Zcyto7 polypeptides from other mammalian species, including murine, porcine, ovine, bovine, canine, feline, equine, and other primates Species orthologs of the human Zcyto7 protein can be cloned using information and compositions provided by the present invention in combination with convention al cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A protein-encoding cDNA can then be isolated by a variety of methods, such as by probing with a complete or partial human or mouse cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the protein. Similar techniques can also be applied to the isolation of genomic clones. As used and claimed the language "an isolated polynucleotide which encodes a polypeptide, said polynucleotide being defined by SEQ ID NO: 2" includes all allelic variants and species orthologs of the polypeptide of SEQ ID NO:2.

The present invention also provides isolated protein polypeptides that are substantially homologous to the protein polypeptides of SEQ ID NO: 2 and its species orthologs. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequence shown in SEQ ID NO:2,or its species orthologs. Such polypeptides will more preferably be at least 90% identical, and most preferably 95% or more identical to SEQ ID NO:2,or its species orthologs. Percent sequence identity is determined by conventional methods. See, for example, Altschul et al., Bull. Math. Bio. 48: 603–616 (1986) and Henikoff and Henikoff, Proc. Natl. Acad. Sci. USA 89:10915–10919 (1992). Briefly, two amino acid sequences are aligned to optimize the alignment scores using a gap opening penalty of 10, a gap extension penalty of 1, and the "blossom 62" scoring matrix of Henikoff and Henikoff (ibid.) as shown in Table 2 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 3) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A [Nilsson et al., EMBO J. 4:1075 (1985); Nilsson et al., Methods Enzymol. 198:3, (1991)], glutathione S transferase [Smith and Johnson, Gene 67:31, (1988)], or other antigenic epitope or binding domain. See, in general Ford et al., Protein Expression and Purification 2: 95–107 (1991. DNAs encoding affinity tags are available from commercial suppliers (e.g., Pharmacia Biotech, Piscataway, N.J.).

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

TABLE 3

Conservative amino acid substitutions

| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |

TABLE 3-continued

Conservative amino acid substitutions

| | |
|---|---|
| Aromatic: | phenylalanine |
| | tryptophan |
| | tyrosine |
| Small: | glycine |
| | alanine |
| | serine |
| | threonine |
| | methionine |

Essential amino acids in the polypeptides of the present invention can be identified according to procedures known in the art, such as site-directed mutagenesis or alanine-scanning mutagenesis [Cunningham and Wells, Science 244: 1081–1085 (1989); Bass et al., Proc. Natl. Acad. Sci. USA 88:4498–4502 (1991)]. In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. See, for example, de Vos et al., Science 255:306–312 (1992); Smith et al., J. Mol. Biol. 224:899–904, 1992; Wlodaver et al., FEBS Lett. 309:59–64 (1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer, Science 241:53–57 (1988) or Bowie and Sauer, Proc. Natl. Acad. Sci. USA 86:2152–2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display, e.g., Lowman et al., Biochem. 30:10832–10837 (1991); Ladner et al., U.S. Pat. No. 5,223,409; Huse, WIPO Publication WO 92/06204) and region-directed mutagenesis, Derbyshire et al., Gene 46:145 (1986); Ner et al., DNA 7:127 (1988).

Mutagenesis methods as disclosed above can be combined with high-throughput screening methods to detect activity of cloned, mutagenized proteins in host cells. Preferred assays in this regard include cell proliferation assays and biosensor-based ligand-binding assays, which are described below. Mutagenized DNA molecules that encode active proteins or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to SEQ ID NO:2 or allelic variants thereof and retain the properties of the wild-type protein. As expressed and claimed herein the language, "a polypeptide as defined by SEQ ID NO: 2" includes all allelic variants and species orthologs of the polypeptide.

Another embodiment of the present invention provides for a peptide or polypeptide comprising an epitope-bearing portion of a polypeptide of the invention. The epitope of the this polypeptide portion is an immunogenic or antigenic epitope of a polypeptide of the invention. A region of a protein to which an antibody can bind is defined as an "antigenic epitope". See for instance, Geysen, H. M. et al., Proc. Natl. Acad Sci. USA 81:3998–4002 (1984).

As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See Sutcliffe, J. G. et al. Science 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer soluble peptides, especially those containing proline residues, usually are effective.

Antigenic epitope-bearing peptides and polypeptides of the invention are therefore useful to raise antibodies, including monoclonal antibodies, that bind specifically to a polypeptide of the invention. Antigenic epitope-bearing peptides and polypeptides of the present invention contain a sequence of at least nine, preferably between 15 to about 30 amino acids contained within the amino acid sequence of a polypeptide of the invention. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that react with the protein. Preferably, the amino acid sequence of the epitope-bearing peptide is selected to provide substantial solubility in aqueous solvents (i.e., the sequence includes relatively hydrophilic residues and hydrophobic residues are preferably avoided); and sequences containing proline residues are particularly preferred. All of the polypeptides shown in the sequence listing contain antigenic epitopes to be used according to the present invention, however, specifically designed antigenic epitopes include the peptides defined by SEQ ID NOs: 27–35.

Polynucleotides, generally a cDNA sequence, of the present invention encode the above-described polypeptides. A cDNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;
Cysteine (Cys) is encoded by TGC or TGT;
Aspartic acid (Asp) is encoded by GAC or GAT;
Glutamic acid (Glu) is encoded by GAA or GAG;
Phenylalanine (Phe) is encoded by TTC or TTT;
Glycine (Gly) is encoded by GGA, GGC, GGG or GGT;
Histidine (His) is encoded by CAC or CAT;
Isoleucine (Ile) is encoded by ATA, ATC or ATT;
Lysine (Lys) is encoded by AAA, or AAG;
Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutamine (Gin) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the above-described cDNA. A messenger RNA (mRNA) will encode a polypeptide using the same codons as those defined above, with the exception that each thymine nucleotide (T) is replaced by a uracil nucleotide (U).

The protein polypeptides of the present invention, including full-length proteins, protein fragments (e.g. receptor-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A Laboratory Manual, (2nd ed.) (Cold Spring Harbor Laboratory Press, Cold Spring Harbor, N.Y., 1989), and Ausubel et al., ibid.

In general, a DNA sequence encoding a Zcyto7 polypeptide is operably linked to other genetic elements required for its expression, generally including a transcription promoter and terminator, within an expression vector The vector will also commonly contain one or more selectable markers and one or more origins of replication, although those skilled in the art will recognize that within certain stems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcyto7 polypeptide into the secretory pathway of a host cell, a secretory signal sequence (also known as a leader sequence, prepro sequence or pre sequence) is provided in the expression vector. The secretory signal sequence may be that of the protein, or may be derived from another secreted protein (e.g., t-PA) or synthesized de novo. The secretory signal sequence is joined to the Zcyto7 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection, Wigler et al., Cell 14:725 (1978); Corsaro and Pearson, Somatic Cell Genetics 7:603 (1981): Graham and Van der Eb, Virology 52:456 (1973), electroporation, Neumann et al., EMBO J. 1:841–845 (1982), DEAE-dextran mediated transfection, Ausubel et al., eds., Current Protocols in Molecular Biology (John Wiley and Sons, Inc., NY, 1987), and liposome-mediated transfection (Hawley-Nelson et al., Focus 15:73 (1993); Ciccarone et al., Focus 15:80 (1993). The production of recombinant polypeptides in cultured mammalian cells is disclosed, for example, by Levinson et al., U.S. Pat. No. 4,713,339; Hagen et al., U.S. Pat. No. 784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 [ATCC No. CRL 1573; Graham et al., J. Gen. Virol. 36:59–72 (1977)] and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. The use of *Agrobacterium rhizogenes* as a vector for expressing genes in plant cells has been reviewed by Sinkar et al., J. Biosci. (Bangalore) 11:47–58 (1987).

Fungal cells, including yeast cells, and particularly cells of the genus Saccharomyces, can also be used within the present invention, such as for producing protein fragments or polypeptide fusions. Methods for transforming yeast cells with exogenous DNA and producing recombinant polypeptides therefrom are disclosed by, for example, Kawasaki, U.S. Pat. No. 4,599,31 1; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845, 075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al., U.S. Pat. No. 4,931,373, which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., J. Gen. Microbiol. 132:3459–3465 (1986) and Cregg, U.S. Pat. No. 4,882,279. Aspergillus cells may be utilized according to the methods of McKnight et al., U.S. Pat. No. 4,935,349 Methods for transforming *Acremonium chrysogenum* are disclosed by Sumino eta., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example drug selection or deficiency in an essential nutrient which is complemented by the selectable marker carried on the expression vector or co-transfected into the host cell.

Within one aspect of the present invention, a novel protein is produced by a cultured cell, and the cell is used to screen for a receptor or receptors for the protein, including the natural receptor, as well as agonists and antagonists of the natural ligand.

Protein Isolation

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, Affinity Chromatography: Principles & Methods (Pharmacia LKB Biotechnology, Uppsala, Sweden, 1988).

The polypeptides of the present invention can be isolated by exploitation of their properties. For example, immobilized metal ion adsorption (IMAC) chromatography can be used to purify histidine-rich proteins. Briefly, a gel is first charged with divalent metal ions to form a chelate [E. Sulkowski, Trends in Biochem. 3:1–7 (1985)]. Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography [Methods in Enzymol., Vol. 182:529–39, "Guide to Protein Purification", M. Deutscher, (ed.), (Acad. Press, San Diego, 1990). Alternatively, a fusion of the polypeptide of interest and an affinity tag (e.g., polyhistidine, maltose-binding protein, an immunoglobulin domain) may be constructed to facilitate purification. Furthermore, to facilitate purification of the secreted receptor polypeptide, an amino or carboxyl-terminal extension, such as a poly-histidine tag, substance P, FLAG® peptide [Hopp et al., Bio/Technology 6:1204–1210 (1988); available from Eastman Kodak Co., New Haven, Conn.), a Glu-Glu affinity tag [Grussenmeyer et al., Proc. Natl. Acad. Sci. USA 82:7952–4 (1985)], or another polypeptide or protein for which an antibody or other specific binding agent is available, can be fused to Zyto7 to aid in purification.

Uses

Northern blot analysis of the expression of Zcyto7 reveals that Zcyto7 is specifically expressed in the spinal cord. In situ analysis of the spinal cord reveals that this expression is localized in the neurons and dorsal root ganglia. Therefore, Zcyto7 may play a role in the maintenance of spinal cord involving either glial cells or neurons. This indicates that Zcyto7 can be used to treat a variety of neurodegenerative diseases such as amyotrophic lateral sclerosis (ALS), or dymyelinating diseases including multiple sclerosis. Zcyto7 may also be used to treat sensory neuropathis. The tissue specificity of Zcyto7 expression suggests that Zcyto7 may be a growth and/or maintenance factor in the spinal cord.

Zcyto7 gene's location on chromosome 5 indicates that zcyto7 is a cytokine which can be used to modulate the activities of cells of the immune system. Zcyto7 can also be used as a chemoattractant of neutrophils in the spinal column. This would be useful as an anti-infective for infections in the spinal column. It could also be used to help regulate other cytokines in the spinal cord. Zcyto7 may also be administered to treat peripheral neuropathies such as Charcot-Marie-Tooth (CMT) disease which is localized to the same chromosomal region of 5q as Zcyto7.

The fact that Zcyto7 inhibits the growth of BAF-3 and TF-1 cells as shown in examples 11 and 12 below indicates that Zcyto7 can be used to treat autoimmune diseases and possibly such cancers such as leukemias.

The present invention also provides reagents which will find use in diagnostic applications. For example, the Zcyto7 gene is heavily expressed in the spinal cord. A probe comprising the Zcyto7 DNA or RNA or a subsequence thereof can be used to determine if the Zcyto7 gene is present on chromosome 5 or if a mutation has occurred.

The present invention also provides reagents with significant therapeutic value. The Zcyto7 polypeptide (naturally occurring or recombinant), fragments thereof, antibodies and anti-idiotypic antibodies thereto, along with compounds identified as having binding affinity to the Zcyto7 polypeptide, should be useful in the treatment of conditions associated with abnormal physiology or development, including abnormal proliferation, e.g., cancerous conditions, or degenerative conditions. For example, a disease or disorder associated with abnormal expression or abnormal signaling by a Zcyto7 polypeptide should be a likely target for an agonist or antagonist of the Zcyto7 polypeptide.

In particular, Zcyto7 can be used to treat inflammation. Inflammation is a result of an immune response to an infection or as an autoimmune response to a self-antigen.

Treatment dosages should be titrated to optimize safety and efficacy. Methods for administration include intravenous, peritoneal, intramuscular, subdural, into the spinal fluid or transdermal administration. Pharmaceutically acceptable carriers will include water, saline, buffers to name just a few. Dosage ranges would ordinarily be expected from 0.1 $\mu$g to 1 mg per kilogram of body weight per day. Preferably, 1 $\mu$g to 100 $\mu$g per day. However, the doses by be higher or lower as can be determined by a medical doctor with ordinary skill in the art. For a complete discussion of drug formulations and dosage ranges see Remington's Pharmaceutical Sciences, 17$^{th}$ Ed., (Mack Publishing Co., Easton, Penn., 1990), and Goodman and Gilman's: The Pharmacological Bases of Therapeutics, 9$^{th}$ Ed. (Pergamon Press 1996).

Use of Zcyto7 to Promote Bone and Cartilage Growth

It has been discovered that Zcyto7 stimulates the proliferation of both chondrocytes and osteoblasts as is shown below in Examples 7 and 9 respectively. In addition, Zcyto7 also stimulates the steady state level of glycosaminoglycan present in chondrocyte cultures as shown in Example 8. Thus Zcyto7 can be used to stimulate both bone and cartilage growth in a variety of different therapeutic settings.

Zcyto7 can be implanted in a mammalian body so that the zcyto7 is in contact with osteoblasts such that osteoblast proliferation occurs and bone growth is stimulated. For example, zcyto7 can be placed in a matrix [with or without a bone morphogenic protein (BMP)]. The BMP induces the migration of mesenchymal osteoblast precursors to the site and further induces differentiation of the mesenchymal cells into osteoblast. Zcyto7 will then stimulate the further proliferation of the osteoblasts. A suitable matrix is made up of particles of porous materials. The pores must be of a dimension to permit progenitor cell migration and subsequent differentiation and proliferation. An ideal particle size should be in the range of 70–850 mm, preferably 150–420 mm. The matrix containing the zcyto7 can be molded into a shape encompassing a bone defect. Examples of matrix materials are particulate, demineralized, guanidine extracted, species-specific bone. Other potentially useful matrix materials include collagen, homopolymers and copolymers of glycolic acid and lactic acid, hydroxyapatite, tricalcium phosphate and other calcium phosphates. Zcyto7 can be applied into a matrix at a sufficient concentration to promote the proliferation of osteoblasts, preferably at a concentration of at least 1 $\mu$g/ml of matrix. A solution of zcyto7 can also be injected directly into the site of a bone fracture or defect including areas of bone degeneration to expedite healing of the fracture or defect site. Examples of BMPs and the use of matrices to produce are disclosed in PCT application publication number WO 92/07073, publication No. WO 91/05802, U.S. Pat. Nos. 5,645,591 and 5,108,753.

Zcyto7 can be further used to treat osteoporosis by administering a therapeutically effective amount of zcyto7 to an individual. A preferred dosage would be 1 $\mu$g of zcyto7 per kilogram of body weight per day.

As stated above, it has also been determined that zcyto7 can be used to promote the production of cartilage through its ability to stimulate the proliferation of chondrocytes. Zcyto7 can be injected directly into the site where cartilage is to be grown. For example, zcyto7 can be injected directly in joints which have been afflicted with osteoarthritis or other injured joints in which the cartilage has been worn down. An example of a case in which additional cartilage needs to be grown is shoulders and knees of injured athletes.

Cartilage can also be grown by first removing chondrocytes from an individual, culturing the chondrocytes with zcyto7 so that they proliferate and reimplanting the chondrocytes back into the individual where cartilage needs to be produced.

Zcyto7 can also be used to stimulate the regeneration of dentin or bone which has been lost due to periodontal disease. To do this, the surrounding tissue should be thoroughly cleaned and a solution of Zcyto7 be administered, preferably by injection, into the site in which dentin regeneration is desired.

Antibodies to the zcyto7 polypeptide can be purified and then administered to a patient. These reagents can be combined for therapeutic use with additional active or inert ingredients, e.g., in pharmaceutically acceptable carriers or diluents along with physiologically innocuous stabilizers and excipients. These combinations can be sterile filtered and placed into dosage forms as by lyophilization in dosage vials or storage in stabilized aqueous preparations. This invention also contemplates use of antibodies, binding fragments thereof or single-chain antibodies of the antibodies including forms which are not complement binding.

The quantities of reagents necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, or transdermal administration. Pharmaceutically Acceptable carriers will include water, saline, buffers to name just a few. Dosage ranges would ordinarily be expected from 1 $\mu$g to 1000 $\mu$g per kilogram of body weight per day. However, the doses may be higher or lower as can be determined by a medical doctor with ordinary skill in the art. For a complete discussion of drug formulations and dosage ranges see Remington's Pharmaceutical Sciences, 17$^{th}$ Ed., (Mack Publishing Co., Easton, Penn., 1990), and Goodman and Gilman's: The Pharmacological Bases of Therapeutics, 9$^{th}$ Ed. (Pergamon Press 1996).

Nucleic Acid-based Therapeutic Treatment

If a mammal has a mutated or lacks a Zcyto7 gene, the Zcyto7 gene can be introduced into the cells of the mammal. In one embodiment, a gene encoding a Zcyto7 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector [Kaplitt et al., Molec. Cell. Neurosci., 2 :320–330 (1991)], an attenuated adenovirus vector, such as the vector described by Stratford-Perricaudet et al., J. Clin. Invest., 90 :626–630 (1992), and a defective adeno-associated virus vector [Samulski et al., J. Virol., 61:3096–3101 (1987); Samulski et al. J. Virol., 63:3822–3828 (1989)].

In another embodiment, the gene can be introduced in a retroviral vector, e.g., as described in Anderson et al., U.S. Pat. No. 5,399,346; Mann et al., Cell, 33:153 (1983); Temin et al., U.S. Pat. No. 4,650,764; Temin et al., U.S. Pat. No. 4,980,289; Markowitz et al., J. Virol., 62:1120 (1988); Temin et al., U.S. Pat. No. 5,124,263; International Patent Publication No. WO 95/07358, published Mar. 16, 1995 by Dougherty et al.; and Blood, 82:845 (1993).

Alternatively, the vector can be introduced by lipofection in vivo using liposomes. Synthetic cationic lipids can be used to prepare liposomes for in vivo transfection of a gene encoding a marker [Felgner et al., Proc. Natl. Acad. Sci. USA, 84:7413–7417 (1987); see Mackey et al., Proc. Natl. Acad. Sci. USA, 85:8027–8031 (1988)]. The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter [see, e.g., Wu et al., J. Biol. Chem., 267:963–967 (1992); Wu et al., J. Biol. Chem., 263:14621–14624 (1988)].

Zcyto7 polypeptides can also be used to prepare antibodies that specifically bind to Zcyto7 polypeptides. These antibodies can then be used to manufacture anti-idiotypic antibodies. As used herein, the term "antibodies" includes polyclonal antibodies, monoclonal antibodies, antigen-binding fragments thereof such as F(ab')$_2$ and Fab fragments, and the like, including genetically engineered antibodies. Antibodies are defined to be specifically binding if they bind to a Zcyto7 polypeptide with a $K_a$ of greater than or equal to $10^7$/M. The affinity of a monoclonal antibody can be readily determined by one of ordinary skill in the art (see, for example, Scatchard, ibid.).

Methods for preparing polyclonal and monoclonal antibodies are well known in the art (see for example, Sambrook et al., Molecular Cloning: A Laboratory Manual, (Second Edition) (Cold Spring Harbor, N.Y., 1989) and Hurrell, J. G. R., Ed., Monoclonal Hybridoma Antibodies: Techniques and Applications (CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zcyto7 polypeptide may be increased through the use of an adjuvant such as Freund's complete or incomplete adjuvant. A variety of assays known to those skilled in the art can be utilized to detect antibodies which specifically bind to Zcyto7 polypeptides. Exemplary assays are described in detail in Antibodies: A Laboratory Manual, Harlow and Lane (Eds.), (Cold Spring Harbor Laboratory Press, 1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

As would be evident to one o ordinary skill in the art, polyclonal antibodies can be generated by inoculating a variety of warm-blooded animals such as horses, cows, goats, sheep, dogs, chickens, rabbits, mice, hamsters, guinea pigs and rats with a Zcyto7 polypeptide or a fragment thereof. The immunogenicity of a Zcyto7 polypeptide may be increased through the use of an adjuvant, such as alum (aluminum hydroxide) or Freund's complete or incomplete adjuvant. Polypeptides useful for immunization also include fusion polypeptides, such as fusions of Zcyto7 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to Zcyto7 protein or peptide, and selection of antibody display libraries in phage or similar vectors (for instance, through use of immobilized or labeled Zcyto7 protein or peptide). Genes encoding polypeptides having potential Zcyto7 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zcyto7 sequences disclosed herein to identify proteins which bind to Zcyto7. These "binding proteins" which interact with Zcyto7 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zcyto7 "antagonists" to block Zcyto7 binding and sign al transduction in vitro and in vivo.

Antibodies can also be generated gene therapy. The animal is administered the DNA or RNA which encodes Zcyto7 or an immunogenic fragment thereof so that cells of the animals are transfected with the nucleic acid and express the protein which in turn elicits an immunogenic response. Antibodies which then are produced by the animal are isolated in the form of polyclonal or monoclonal antibodies.

Antibodies to Zcyto7 may be used for tagging cells that express the protein, for affinity purification, within diagnostic assays for determining circulating levels of soluble protein polypeptides, and as antagonists to block ligand binding and signal transduction in vitro and in vivo.

Radiation hybrid mapping is a somatic cell genetic technique developed for constructing high-resolution, contiguous maps of mammalian chromosomes [Cox et al., Science 250:245–250 (1990)]. Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The present invention also provides reagents which will find use in diagnostic applications. For example, the Zcyto7 gene has been mapped on chromosome 5q31. A Zcyto7 nucleic acid probe could to used to check for abnormalities on chromosome 5. For example, a probe comprising Zcyto7 DNA or RNA or a subsequence thereof can be used to determine if the Zcyto7 gene is present on chromosome 5q31 or if a mutation has occurred. Detectable chromosomal aberrations at the Zcyto7 gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art [Sambrook et al., ibid.; Ausubel, et. al., ibid.; Marian, A. J., Chest, 108: 255–265, (1995)].

Zcyto7 maps at the 5q31 region which is a "gene cluster" which contains a group of cytokines and cytokine receptors. The cytokines clustered there include IL-3, IL4, IL-5, IL-13, GM-CSF, and M-CSF. This result authenticates zcyto7 as a cytokine.

The invention is further illustrated by the following non-limiting examples.

EXAMPLE 1

Cloning of Zcyto7

Zcyto7 was identified from expressed sequence tag defined (EST) 582069 (SEQ ID NO: 3) by its homology to Interleukin-17. The EST 582069 cDNA clone was obtained from a human fetal heart cDNA library from the IMAGE consortium, Lawrence Livermore National Laboratory through Genome Systems, Inc. The cDNA was supplied as an agar stab containing *E. coli* transfected with the plasmid having the cDNA of interest. The plasmid containing the cDNA was streaked out on an LB 100 µg/ml ampicillin and 100 µg/ml methicillin plate. The cDNA insert was sequenced. The insert was determined to be 717 base pairs long with a 180 amino acid open reading frame and a putative 20 amino acid signal peptide.

EXAMPLE 2

Northern Blot Analysis

Human multiple tissue blots 1,2,3 (Clontech)were probed to determine the tissue distribution of Zcyto7. A EcoRI/NotI fragment containing the entire Zcyto7 coding region was generated from the EST582069 clone and used for the probe. A plasmid prep of EST582069 was prepared from a 5 ml LB 100 µg/ml ampicillin overnight culture at 37° using the QIAprep Spin Miniprep Kit (Qiagen). 12 µl out of 100 µl were digested with 5 µl of H buffer (Boehringer Mannheim), 12.5 units of EcoRI (Gibco BRL) and 12.5 units Not1 (New England Biolabs) in a 50 µl reaction at 37° C. for 2 hours. The digest was electrophoresed on a 0.7% TBE agarose gel and the fragment was cut out. To obtain additional material the digest was repeated under the same conditions as above except 24 µl of EST582069 was used in the second digest. The second digest was electrophoresed on a 0.7% TBE agarose gel and the fragment was cut out. The DNA was extracted from both gel slabs with a QIAquick Gel Extraction Kit (Qiagen). 135 ng of this DNA was labeled with $P^{32}$ using the Multiprime DNA Labeling System (Amersham) and unincorporated radioactivity was removed with a Nuc-Trap Probe Purification Column (Stratagene). Multiple tissue northerns and a human RNA master blot were prehybridized 3 hours with 10 ml ExpressHyb Solution (Clontech) containing 1 mg salmon sperm DNA which was boiled 5 minutes and then iced 1 minute and added to 10 ml of ExpressHyb Solution, mixed and added to blots. Hybridization was carried out overnight at 65° C. Initial wash conditions were as follows: 2×SSC, 0.05% SDS RT for 40 minutes with several changes of solution then 0.1×SSC 0.1% SDS at 50° C. for 40 minutes, 1 solution change. Blots were than exposed to film a −80° C. for 5 hours. There was cross hybridization/background so blots were further washed at 55° C. then 65° C. with 0.1%×SSC, 0.1% SDS for 1 hour each. Spinal cord showed very high expression of Zcyto7 mRNA and trachea showed weak expression of mRNA. The transcript size was approximately 0.75 kb.

EXAMPLE 3

Chromosomal Assignment and Placement of Zcyto7

Zcyto7 was mapped to chromosome 5 using the commercially available "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map of the human genome) which was constructed with the GeneBridge 4 Radiation Hybrid Panel.

For the mapping of Zcyto7 with the "GeneBridge 4 RH Panel", 20µl reactions were set up in a PCRable 96-well microtiter plate (Stratagene, La Jolla, Calif.) and used in a "RoboCycler Gradient 96" thermal cycler (Stratagene). Each of the 95 PCR reactions consisted of 2µl 10×KlenTaq PCR reaction buffer (CLONTECH Laboratories, Inc., Palo Alto, Calif.), 1.6µldNTPs mix (2.5 mM each, PERKIN-ELMER, Foster City, Calif.), 1µl sense primer SEQ ID NO:4, 1µl antisense primer SEQ ID NO:5, 2µl "RediLoad" (Research Genetics, Inc., Huntsville, Ala.), 0.4µl 50× Advantage KlenTaq Polymerase Mix (Clontech Laboratories, Inc.), 25 ng of DNA from an individual hybrid clone or control and x µl ddH$_2$O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 52° C. and 1 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that Zcyto7 maps 490.89 cR from the top of the human chromosome 5 linkage group on the WICGR radiation hybrid map. Relative to the centromere, its nearest proximal marker was D5S413 and its nearest distal marker was WI-5208. The use of surrounding markers position Zcyto7 in the 5q31.3–q32 region on the integrated LDB chromosome 5 map (The Genetic Location Database, University of Southhampton, WWW server: http://cedar.genetics.soton.ac.uk/public_html/).

EXAMPLE 4

Construction of Zcyto7 Expression Vectors

Two Zcyto7 construction vectors were made in a FLAG amino acid sequence (SEQ ID NO: 10) was inserted onto the N-terminal or C-terminal ends of the Zcyto7 polypeptide. For the construction in which the FLAG amino acid sequence was attached to the N-terminus of Zcyto7, a 473 bp Zcyto7 PCR DNA fragment was generated with 1 µl of a dilution of the EST582069 plasmid prep of Example 2 and 20 picomoles (pm) of primer SEQ ID NO: 6 and 20 pm primer SEQ ID NO: 7. The PCR reaction was incubated at 94° C. for 1 minute, and then run for 5 cycles each individual cycle being comprised of 20 seconds at 94° C. and 2 minutes at 64° C. This was followed by 22 cycles each cycle being comprised of 20 seconds at 94° C. and 2 minutes at 74° C. The reaction was ended with an incubation for 10 minutes at 74° C. 50 µl of the PCR reaction mixture was digested with 30 units of BamH1 (Boehringer Mannheim) and 120 units of Xho1 (Boehringer Mannheim) for 2 hours at 37° C. The digested reaction mixture was electrophoresed on a 1% TBE gel; the DNA band was excised with a razor blade and the DNA was extracted from the gel with the Qiaquick<<Gel Extraction Kit (Qiagen). The excised DNA was subcloned into plasmid nfpzp9 which had been cut with Bam and Xho. Nfpzp9 is a mammalian cell expression vector comprising an expression cassette containing the mouse metallothionein-1 promoter, a sequence encoding the tissue plasminogen activator (TPA) leader, then the FLAG peptide (SEQ ID NO: 10), then multiple restriction sites. These were followed by the human growth hormone terminator, an *E. coli* origin of replication and a mammalian selectable marker expression unit containing the SV40 promoter, enhancer and origin of replication; a dihydrofolate reductase gene (DHFR) and the SV40 terminator.

For the construction of the zcyto7 gene in which a C-terminus FLAG was inserted onto the C-terminus of the zcyto7 polypeptide, a 543 bp zcyto7 PCR fragment was generated with 1 µl of dilution of the EST582069 plasmid preparation described in Example 1 and 20 pm each of primers SEQ ID NO: 8 and SEQ ID NO: 9. The PCR reaction was incubated at 94° C. for 1 minute, then run for 5 cycles, each cycle being comprised 20 seconds at 94° C. and 2 minutes at 55° C. This was followed by 22 cycles each cycle comprised of 20 seconds at 94° C. and 2 minutes at 74° C. The reaction was ended with a final 10 minute extension at 74° C. The entire reaction mixture was run on a 1% TBE gel and the DNA was cut out with a razor blade and the DNA was extracted using the QIAQUICK™ gel extraction kit. 20 µl out of the recovered 35 µl digested with 10 units of BamH1 (Boehringer Mannheim) and 10 units of EcoR1 (Gibco BRL) for 2 hours at 37° C. The digested PCR mixture was electrophoresed on a 1% TBE gel. The DNA band was cut out with a razor blade and the DNA was extracted from the gel using the QIAquick<<Gel Extraction Kit (Qiagen). The extracted DNA was subcloned into plasmid cfpzp9 which had been cut with EcoR1 and BamH1. Plasmid cfpzp9 is a mammalian expression vector containing an expression cassette having the mouse metallothionein-1 promoter, multiple restriction sites for insertion of coding sequences, a sequence encoding the FLAG peptide, SEQ ID NO:10, a stop codon, a human growth hormone terminator, an *E. coli* origin of replication, a mammalian selectable marker expression unit having an SV40 promoter, enhancer and origin of replication, a DHFR gene and the SV40 terminator.

Using antibodies to the FLAG polypeptides, one can separate the FLAG-tagged Zcyto7 polypeptides from a cell supernatant liquid.

EXAMPLE 5

Cloning of Murine Zcyto7

Mouse Zcyto7 was identified from EST 660242 SEQ ID NO: 14 by its homology to human Zcyto7. The cDNA clone was obtained from Lawrence Livermore National Laboratory through Genome Systems from a murine embryo cDNA library in which the embryos were between 13.5 and 14.5 days old. The cDNA was supplied as an agar stab containing E. coli transfected with the plasmid having the cDNA of interest and then streaked out on an LB 100 µg/ml ampicillin, 25 µg/ml methicillin plate. The cDNA insert in EST660242 was sequenced. The insert was determined to be 785 base pairs with an open reading frame of 180 amino acids and a putative 20 amino acid signal peptide. The sequences are defined by SEQ ID NO:11 and SEQ ID NO:12.

EXAMPLE 6

Tissue Distribution of Murine Zcyto7

Mouse Multiple Tissue Northern Blot (Clontech, Palo Alto, Calif.), mouse northern dot blot (Clontech), a mouse embryo northern blot, and a mouse spinal cord dot blot were probed to determine the tissue distribution of murine Zcyto7.

The mouse embryo RNA were isolated from mouse embryos which were 6 to nine days from the date of fertilization using the POLY (A) PURE® mRNA isolation kit (Ambion). 100 mg of each mouse embryo was lysed in 1 ml of lysis buffer, homogenized and processed in batch method according to the manufacturer's protocol. For the northern blot, 2 µg of RNA was loaded on 1.5% agarose, 2.2M formaldehyde gel. The gel was run at 60V for four hours and 30 minutes. The RNA was transferred overnight onto a Nytran membrane which had been pre-wetted in 20xSSC. The RNAs were crosslinked onto the membrane by UV light and baked at 80° C. for 1 hour.

The mouse spinal cord RNA was also prepared with the POLY (A) PURE® mRNA isolation kit (Ambion). The mouse spinal cord dot blot was made by spotting a dot with 1, 2 and 3 µl of RNA at 1 µg RNA/µl concentration onto Nytran membrane.

A Not1/EcoRI fragment containing the entire Zcyto7 coding region was generated from the clone containing SEQ ID NO: 12 (hereinafter referred to as the SEQ ID NO:12 clone) and was used for the probe. A plasmid prep of the SEQ ID NO:12 clone was prepared from a 5 ml LB 100 µg/ml ampicillin overnight culture at 37° C. using the QIAPREP SPIN MINIPREP kit (Qiagen). 4.66 µg were digested with 8 µl of high buffer (Boehringer Mannheim), 20 units of Not1 (Biolabs) and 20 units of EcoRI (Gibco BRL) in a 80 µl reaction at 37° C. for 2 hours. The digest was electrophoresed on a 1.0% TBE gel and the fragment was cut out. The DNA was extracted from the gel slab with a QIAQUICK® gel extraction kit (Qiagen). 98.8 ng of this fragment was labeled with $P^{32}$ using the MULTIMPRIME® DNA labeling system (Amersham) and unincorporated radioactivity was removed with a NUCTRAP® probe purification column (Stratagene).

The two northern preps and the two dot blot preps were prehybridized for 3 hours at 65° C. as follows. 1 mg of salmon sperm was boiled 5 minutes, iced 1 minute, mixed with 10 ml of EXPRESSHYB® solution and added to the blots. Hybridization was carried out overnight at 65° C. Initial wash conditions were as follows: 2xSSC, 0.1% SDS for 40 minutes at room temperature then 0.1xSSC, 0.1% SDS for 40 minutes at 50° C. Blots were exposed to film overnight at −80° C. The northern blots and the mouse dot blot were further washed with 0.1%xSSC, 0.1% SDS at 60° C. to remove background. The mouse spinal cord dot blot was washed again at higher stringency with 0.1xSSC, 0.1% SDS at 65° C. to confirm the earlier results. Results: Mouse Zcyto7 expression was seen in the spinal cord, submaxillary gland and epididymis. Mouse embryo showed expression of Zcyto7 starting on day 12, peaking at day 16 and ending day 17 from the date of fertilization. The transcript size was approximately 1 kb.

EXAMPLE 7

Proliferation of Chondrocytes Using Zcyto7

A chondrocyte proliferation assay was done to determine the effect that Zcyto7 would have on chondrocyte proliferation. The assay was done with 20% confluent cultures. As a control vehicle, bovine serum albumin was added to a culture of chondrocytes instead of Zcyto7. The assay measured the 3H-thymidine incorporation of nascent DNA in the chondrocytes, Wahl et al., Mol. Cell. Biol. 8:5016–5025 (1988).

Results: A 3.5–9 fold stimulation of primary chondrocyte proliferation was seen upon exposure of the chondrocyte cultures to 1 µg/ml of zcyto7. Chondrocyte stimulation by zcyto7 was seen with multiple preparations of the protein and was seen across species lines. It contrast to this, the control experiment using BSA resulted in no stimulation of chondrocytes.

EXAMPLE 8

Production of Glycosaminoglycan by Zcyto7-treated Chondrocytes

A 20% confluent culture of chondrocytes was prepared and zcyto7 was applied at a concentration of 1 g/ml. In a second experiment in addition to zcyto7, IL-1β was applied to the cell culture. In a control group BSA was added to the chondrocyte culture. The level of glycosaminoglycan (GAG) production by the chondrocyte culture was then determined using a 1,9-dimethylmethlyene blue dye binding assay, Fardale et al., Biochem. Biophys. Acta 888:173–177 (1987).

Results: Chondrocytes which were cultured with zcyto7 showed a 50% increase in the steady state presence of GAG in the chondrocyte culture. Moreover, when the chondrocytes were co-cultured with both zcyto7 and interleukin-1β (IL-1) the GAG production by the chondrocytes increased 2.5 fold as compared with culturing of the chondrocytes with either zcyto7 or IL-1β alone. While the cultured cells to which BSA was added showed no increased production of GAG.

EXAMPLE 9

Osteoblast Stimulation by Zcyto7

The CCC4 cell line is an osteoblast-like cell line derived from p53 knockout mice. The CCC4 line was transfected with a plasmid containing an inducible serum response element (SRE) driving the expression of luciferase. The stimulation of the SRE and thus the expression of luciferase indicates that the chemical entity is likely to stimulate osteoblasts.

CCC4 cells were cultured in the presence of 1 µg of zcyto7/ml of culture medium. As a control BSA, fibroblast growth factor (FGF) and platelet-derived growth factor (PDGF) were each added to different cultures of CCC4 cells. BSA was a negative control and FGF and PDGF were positive controls as they are known to promote osteoblast proliferation. Luciferase activity was detected by addition of 40 μl of Promega luciferase substrate using a 2 second integrated read on Labsystes LUMINOSKAN<<.

Results: Zcyto7 as well as, FGF and PDGF stimulate the expression of luciferase in this assay indicating that they stimulate osteoblasts. The BSA vehicle control was negative in this assay.

EXAMPLE 10

Effect of Zcyto7 on the Growth of Fibroblasts

Confluent cultures of human dermal, lung, and fetal lung fibroblasts were inoculated with Zcyto7 to determine the effects of Zcyto7 on the growth of fibroblasts. FGF was used as a positive control and BSA as a negative control vehicle. Results: Zcyto7 had no effect on the growth of fibroblasts.

EXAMPLE 11

Effect of Zcyto7 on the Growth of BaF3 Cells

BaF3 cells, a murine pre-B cell line dependent on IL-3 to proliferate, were washed several times with base medium and then plated in a 96-well plate each well contained approximately 5500 cells/well. The cells were treated with either 1 μg/ml of Zcyto7 or 1–2 pg/ml of L-3 or with a combination of both Zcyto7 and IL-3. Also in a separate experiment 0.1–10 ng/ml of TGFβ was added to the wells instead of Zcyto7. After incubation of the assay plate at 37° C. and 5% CO2 for 3–6 days, 20 μl of ALAMAR blue was added to each well and the plate is incubated at 37° C. for 15–24 hours. The plate was then read with a fluorometer with excitation wavelength of 544 m and emission wavelength of 590 m. The assay was also scored by eye for stimulation or inhibition of cell proliferation prior to the addition of the ALAMAR blue. The base medium contained RPMI 1640+10% HIA-FBS+L-glutamine+Na pyruvate.

Results: Zcyto7 and TGFβ significantly inhibited the IL-3 driven proliferation of BaF3 cells. However, when neutralizing antibodies to TGFβ were added in along with the Zcyto7, the Zcyto7 inhibition of the proliferation of the BaF3 cells was eliminated.

EXAMPLE 12

Effect of Zcyto7 on the Growth of TF-1 Cells

TF-1 cells, a human leukemia cell line which is GM-CSF or IL-1β dependent, were washed several times with base medium and then plated in a 96-well plate each well containing approximately 7000 cells/well. The cells were co-cultured with 1 μg/ml of Zcyto7 and 100–200 pg/ml of IL-1β. Also in a separate experiment TGFβ was added to the wells instead of Zcyto7. After incubation of the assay plate at 37° C. and 5% CO2 for 3–6 days, 20 μl of ALAMAR blue was added to each well and the plate is incubated at 37° C. for 15–24 hours. The plate is then read with a fluorometer with excitation wavelength of 544 nm and emission wavelength of 590 nm. The assay was also scored by eye for stimulation or inhibition of cell proliferation prior to the addition of the ALAMAR blue. The base medium contained RPMI 1640+10% HIA-FBS+L-glutamine+Na pyruvate.

Results: The IL-1β stimulation of TF-1 cells is inhibited by both Zcyto7 and TGF-β. The concentration of Zcyto7 at which inhibition of proliferation occurred was greater than 200 ng/ml; and the concentration of TGF-β at which inhibition of proliferation occurred was about 50 pg/ml.

We claim:

1. An isolated polypeptide comprised of the amino acid sequence of SEQ ID NO: 36 wherein the end terminal phenylalanine at amino acid residue 158 is absent.

2. An isolated polypeptide comprised of the amino acid sequence of SEQ ID NO: 36.

* * * * *